United States Patent [19]
Bell et al.

[11] Patent Number: 5,575,789
[45] Date of Patent: Nov. 19, 1996

[54] ENERGIZABLE SURGICAL TOOL SAFETY DEVICE AND METHOD

[75] Inventors: Gregory J. Bell; Jeffrey L. Eggleston, both of Broomfield; Kamala J. Grasso; Jenifer S. Kennedy, both of Boulder; Dale Schmaltz, Boulder; Kenneth D. Taylor, Broomfield, all of Colo.

[73] Assignee: Valleylab Inc., Boulder, Colo.

[21] Appl. No.: 330,278

[22] Filed: Oct. 27, 1994

[51] Int. Cl.$^6$ ............................................. A61B 17/36
[52] U.S. Cl. ............................ 606/42; 606/41; 606/32; 606/10
[58] Field of Search ................... 606/10–15, 27–34, 606/37–42, 45–52; 604/21, 22

[56] References Cited

U.S. PATENT DOCUMENTS

| | | | |
|---|---|---|---|
| 4,418,692 | 12/1983 | Guay . | |
| 4,470,414 | 9/1984 | Imagawa et al. | 606/11 |
| 4,573,466 | 3/1986 | Simada et al. | 606/11 |
| 4,608,978 | 9/1986 | Rohr | 606/11 |
| 4,823,791 | 4/1989 | D'Amelio et al. | 606/37 |
| 4,911,159 | 3/1990 | Johnson et al. . | |
| 5,035,695 | 7/1991 | Weber, Jr. et al. . | |
| 5,318,516 | 6/1994 | Cosmescu | 606/34 |
| 5,383,874 | 1/1995 | Jackson et al. | 606/34 |
| 5,443,462 | 8/1995 | Hannant | 606/34 |

*Primary Examiner*—Angela D. Sykes
*Assistant Examiner*—Michael Peffley
*Attorney, Agent, or Firm*—Peter C. Richardson; Lawrence C. Akers; Aaron Passman

[57] ABSTRACT

A surgical safety apparatus for use in connection with an energizable surgical device prevents inadvertent activation of a surgical tool. The energizable surgical device may include an electrosurgical system, a laser scalpel, an ultrasonic aspirator, and combinations thereof. An activation circuit is in connection with the source of energy and in connection with the handpiece. The activation circuit has two states: the first state disconnects the source of energy from the handpiece, the second state connects the source of energy to the handpiece. A sensing element is connected to the activation circuit. The sensing element signals the activation circuit to convert the activation circuit from the first state to the second state. The activation circuit may remain in the second state for a preestablished period of time followed by a reversion to the first state. The activation circuit may include a relay which may be connected to operate accessories including smoke evacuators, lights, videos or irrigators. The sensing element may be disposed to sense the proximity of the surgical tool to the surgical site. The sensing element may be disposed to sense a voice command. The sensing element can monitor the activations of an electrical switch associated with the surgical tool. If the sensing element detected a specified timed pattern of activations of the electrical switch, for example a double click, then the sensing element would signal the activation circuit to convert to the second state.

14 Claims, 2 Drawing Sheets

\# ENERGIZABLE SURGICAL TOOL SAFETY DEVICE AND METHOD

FIELD OF THE INVENTION

This invention pertains to the prevention of inadvertent activation of energizable surgical tools such as an electrosurgical pencil, a laser scalpel, an ultrasonic aspirator or the like, and more particularly a safety switch arrangement.

BACKGROUND OF THE DISCLOSURE

Energizable surgical tools present a safety hazard to the patient and operating room personnel if the tools are unintentionally activated. Accidental contact with an energized surgical tool can result in burns and other tissue damage. The present design of those instruments has not entirely eliminated this hazard, and accidents of this nature may occur under unexpected circumstances.

In a surgical theater, energized surgical tools are used by a surgeon to operate on a patient's tissue and organs. Typical energy sources include high frequency electrical current, laser illumination, and ultrasonic vibration. A switch is typically provided to direct this energy to the surgical tool. The switch may be located on the handpiece of the surgical tool, or at another location such as near the surgeon's foot. Normally the switch is open and when the surgeon wishes to operate the tool, the switch is manually closed. The simple mechanical action on the switch is sufficient to direct energy to the tool.

During surgery, surgical tools are often placed near the surgical site for easy access. This placement may increase the risk of accidentally bumping or keying the switching mechanism. Furthermore, a surgeon may unintentionally activate the tool while it is held during surgery. For example an electrosurgical pencil may be activated by accidental pressure on a rocker switch or foot pedal.

Certain surgical tool designs have attempted to address the problem of inadvertent activation. U.S. Pat. No. 4,418,692 discloses an electrosurgical tool for use in laparoscopic tubal cauterization with electrodes disposed to first grasp tissue. The electrodes can not become energized unless they are in a closed configuration, i.e. about the tissue to be electrosurgically treated. This prevents premature activation of the electrodes since they are normally held in an open configuration. This patent does not address the more general design issue of inadvertently activating any energizable surgical tool.

U.S. Pat. No. 5,035,695 discloses an extendable electrocautery surgery apparatus with an interlock switch. The interlock switch is disposed to cut off the application of all electrical signals when the electrode conductor is in a retracted configuration. There are additional switches which select between cutting and coagulation waveforms. These switches are shrouded against inadvertent activation when the electrode conductor is in a retracted configuration.

U.S. Pat. No. 4,911,159 discloses an electrosurgical instrument with an on/off switch that directs power to the electrode conductor. The switch may be on the handpiece of the instrument or on a separate foot-operated device. In addition, there are separate switches for selecting cut or coagulation waveforms.

None of the above disclosures teaches the safety apparatus of the present invention, which may be used in connection with any energizable surgical device.

SUMMARY OF THE INVENTION

It is the general object of the invention to provide a surgical safety apparatus for use in connection with an energizable surgical device. The energizable surgical device may include an electrosurgical system, a laser scalpel, an ultrasonic aspirator, and combinations thereof. The energizable surgical device has a source of energy and a handpiece. The handpiece is designed for connection to the source of energy and held by the surgeon during a surgical procedure. A surgical tool is supported on the handpiece. The safety apparatus is intended to reduce the possibility of inadvertent activation of the surgical tool.

An activation circuit is in connection with the source of energy and in connection with the handpiece. The activation circuit has two states: the first state disconnects the source of energy from the handpiece, the second state connects the source of energy to the handpiece. While the activation circuit is in its first state, the tool on the handpiece may not be energized.

A sensing element is connected to the activation circuit. The sensing element signals the activation circuit to convert the activation circuit from the first state to the second state. The sensing element is designed to detect a situation in which the surgical tool is ready to be used.

An acoustical tone generator in the activation circuit may audibly indicate when the activation circuit has been converted from the first state to the second state, or from the second state to the first state. The activation circuit may remain in the second state for a preestablished period of time followed by a reversion to the first state. The activation circuit may include a relay which may be connected to operate accessories including smoke evacuators, lights, videos or irrigators.

In one embodiment, the sensing element would monitor the activations of an electrical switch associated with the surgical tool. When the activation circuit is in its first state, the electrical switch cannot directly energize the tool. However, if the sensing element detected a specified timed pattern of activations of the electrical switch, for example a double click, then the sensing element would signal the activation circuit to convert to the second state. Once the activation circuit was in the second state, the electrical switch would operate the surgical tool. The electrical switch may also be used to select and operate modes of energy from the source of energy. The electrical switch may also be a foot operated switch.

The sensing element may have an adjustor to set the designated pattern of successive activations of the electrical switch. For example, the time between two successive activations of the electrical switch could be adjusted between one fourth second and three seconds.

It is another object of this disclosure to provide a method for using a surgical safety apparatus. One step may be signalling the activation circuit with the sensing element to convert the activation circuit from the first state to the second state. Then there may be the step of holding the activation circuit in the second state for a preestablished period of time followed by reverting to the first state. There may be the additional step of audibly indicating when the activation circuit has been converted from one state to another. There may also be the step of operating accessories including smoke evacuators, lights, videos or irrigators with a relay connected to the activation circuit.

In the preferred embodiment of the invention, there is a method which includes the step of responding to a designated timed pattern of successive activations of the electrical switch with a sensing element when the activation circuit is in the first state to change the activation circuit from the first state to the second state. There may also be the step of adjusting the sensing element to set the designated pattern of successive activations of the electrical switch. An example of this step may be designating the timed pattern of successive activations of the electrical switch as a pattern wherein the switch is activated twice within a time range of one fourth second to three seconds. Also, there may be the step of connecting the electrical switch to the source of energy to operate various modes of energy from the source of energy. Further, there may be the step of operating the electrical switch with a foot pedal.

DETAILED DESCRIPTION OF THE INVENTION

Figure 1:
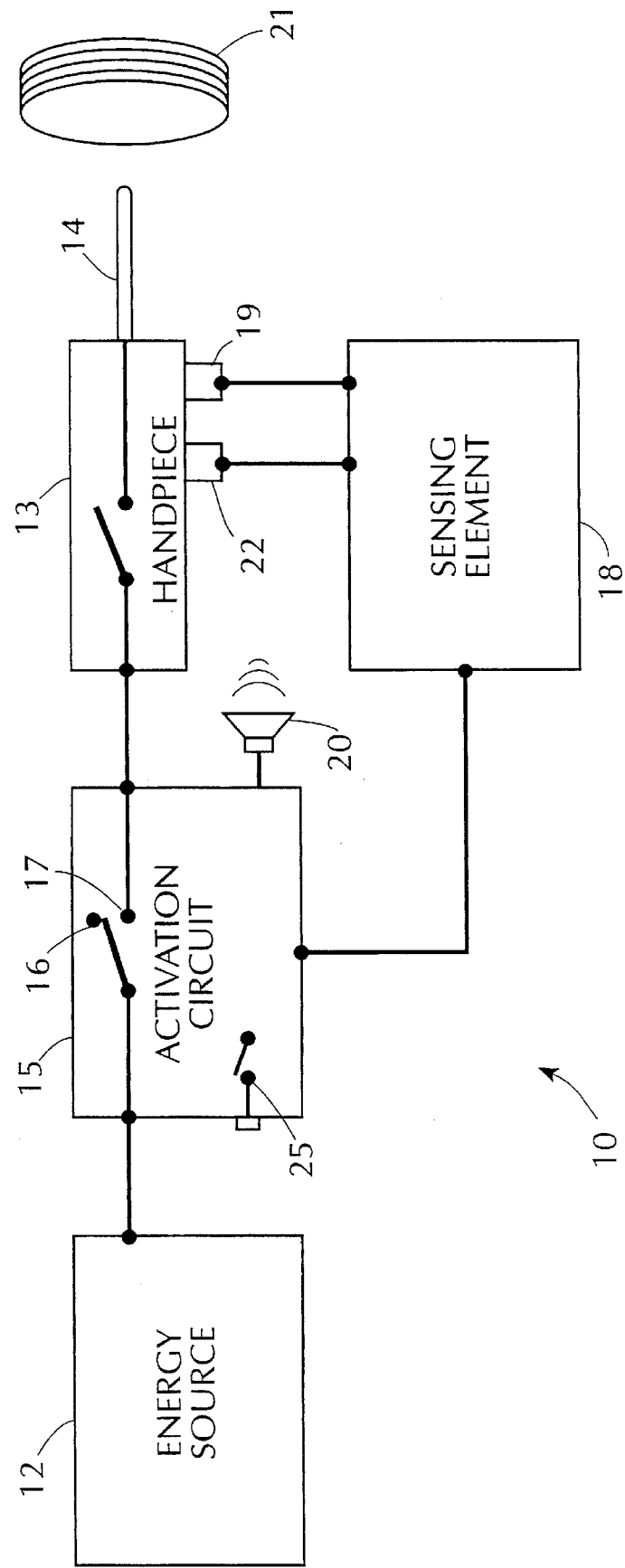
FIG. 1 is a block diagram of a surgical safety apparatus which illustrates several possible embodiments of the invention.

Referring to FIG. 1, there is pictured a surgical safety apparatus 10 for use in connection with an energizable surgical device. The energizable surgical device includes an energy source 12, and a handpiece 13. The energy source 12 may provide electrosurgical energy, laser energy, and ultrasonic energy; the energy source may provide these energy types either individually, concurrently, or in combinations. The handpiece 13 is designed for connection to the energy source 12 and held by the surgeon during a surgical procedure. A surgical tool 14 is supported on the handpiece 13. The safety apparatus is intended to reduce the possibility of inadvertent activation of the surgical tool.

An activation circuit 15 is in connection with the energy source 12 and in connection with the handpiece 13. The activation circuit 15 has two states. The first state of the activation circuit 15 is schematically shown by a position 16 in which the energy source 12 is disconnected from the handpiece 13. The second state of the activation circuit 15 is schematically shown by a position 17 in which the energy source 12 may be connected to the handpiece 13. While the activation circuit 15 is in its first state 16, the tool 14 on the handpiece 13 may not be energized.

An acoustical tone generator 20 in the activation circuit 15 may audibly indicate when the activation circuit 15 has been converted from the first state 16 to the second state 17, or from the second state 17 to the first state 16. The activation circuit 15 may remain in the second state 17 for a preestablished period of time followed by a reversion to the first state 16. The activation circuit 15 may include a relay 25 which may be connected to operate accessories including smoke evacuators, lights, videos or irrigators.

Figure 2:
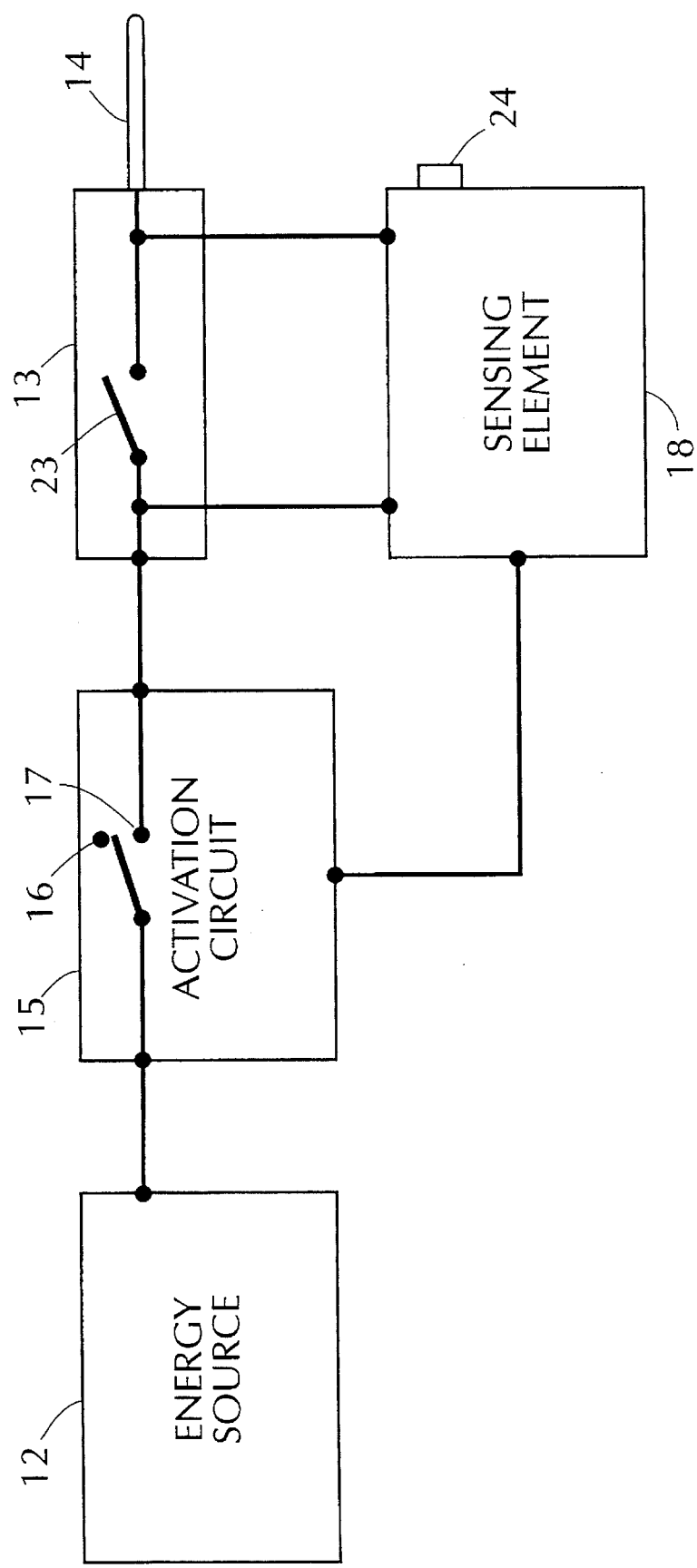
FIG. 2 is a block diagram of a surgical safety apparatus which illustrates the preferred embodiment of the invention.

In one embodiment, shown in FIG. 2, the sensing element 18 would monitor the activations of an electrical switch 23 associated with the surgical tool 14. When the activation circuit is in its first state 16, the electrical switch 23 would not be able to energize the tool 14. However, if the sensing element 18 detected a specified timed pattern of activations of the electrical switch 23, for example two successive activations within one second, then the sensing element 18 would signal the activation circuit 15 to convert to the second state 17. Once the activation circuit 15 was in the second state 17, the electrical switch 23 would operate the surgical tool 14. The electrical switch 23 may also be used to select and operate modes of energy from the energy source 12. The electrical switch 23 may also be a foot operated switch.

The sensing element 18 may have an adjustor 24 to set the designated pattern of successive activations of the electrical switch 23 which will cause the activation circuit 15 to be signalled. For example, the time between two successive activations of the electrical switch 23 could be adjusted between one fourth second and three seconds.

What is claimed is:

1. A surgical safety apparatus comprising:

an energizable surgical device, the energizable surgical device having a source of energy and a handpiece connected thereto, the handpiece having a surgical tool supported thereon;

an activation circuit in connection with the source of energy and in connection with the handpiece, the activation circuit having a first state wherein it disconnects the source of energy from the handpiece, the activation circuit having a second state wherein it connects the source of energy to the handpiece;

an electrical switch attached to the surgical tool, the electrical switch disposed to connect the source of energy to the surgical tool when the activation circuit is in the second state;

a sensing element in the activation circuit responsive to a designated timed pattern of successive activations of the electrical switch to change the activation circuit from the first state to the second state.

2. The apparatus of claim 1 wherein an acoustical tone generator in the activation circuit audibly indicates when the activation circuit has been converted from the first state to the second state.

3. The apparatus of claim 1 wherein an acoustical tone generator in the activation circuit audibly indicates when the activation circuit has been converted from the second state to the first state.

4. The apparatus of claim 1 wherein the activation circuit includes a relay, the relay electrically connected to close whenever the activation circuit is in its second state.

5. The apparatus of claim 1 wherein the source of energy is an electrosurgical generator.

6. The apparatus of claim 1 wherein the source of energy has several modes and the electrical switch is connected to the source of energy to also select and operate modes of energy from the source of energy.

7. The apparatus of claim 1 wherein the electrical switch is a foot operated switch.

8. The apparatus of claim 1 wherein the sensing element has an adjustor to set the designated pattern of successive activations of the electrical switch.

9. The apparatus of claim 1 wherein the designated timed pattern of successive activations of the electrical switch is a pattern wherein the switch is activated twice within a time range of about one fourth second to three seconds.

10. A method for using a surgical safety apparatus having an energizable surgical device, the energizable surgical device including a source of energy and a handpiece connected thereto, the handpiece having a surgical tool supported thereon, the method comprising the steps of:

connecting an activation circuit with the source of energy and with the handpiece, the activation circuit having a first state wherein it disconnects the source of energy from the handpiece, the activation circuit having a second state wherein it connects the source of energy to the handpiece;

connecting the source of energy to the surgical tool with an electrical switch when the activation circuit is in the second state, and responding to a designated timed pattern of successive activations of the electrical switch with a sensing element when the activation circuit is in the first state to change the activation circuit from the first state to the second state.

11. The method of claim 10 with the step of connecting the electrical switch to the source of energy to operate various modes of energy from the source of energy.

12. The method of claim 10 with the step of operating the electrical switch with a foot pedal.

13. The method of claim 10 with the step of adjusting the sensing element to set the designated pattern of successive activations of the electrical switch.

14. The method of claim 10 with the step of designating the timed pattern of successive activations of the electrical switch as a pattern wherein the switch is activated twice within a time range of one fourth second to three seconds.

* * * * *